(12) United States Patent
Smith

(10) Patent No.: US 11,733,225 B2
(45) Date of Patent: Aug. 22, 2023

(54) OXYGEN SENSOR FOR HIGH TEMPERATURE KILNS AND METHOD OF FABRICATION

(71) Applicant: Mark C Smith, Cornelius, OR (US)

(72) Inventor: Mark C Smith, Cornelius, OR (US)

(*) Notice: Subject to any disclaimer, the term of this patent is extended or adjusted under 35 U.S.C. 154(b) by 204 days.

(21) Appl. No.: 17/017,455

(22) Filed: Sep. 10, 2020

(65) Prior Publication Data

US 2022/0074905 A1    Mar. 10, 2022

(51) Int. Cl.
| | |
|---|---|
| G01N 33/00 | (2006.01) |
| F27B 9/40 | (2006.01) |
| G01R 3/00 | (2006.01) |
| G01N 27/04 | (2006.01) |
| F27B 9/30 | (2006.01) |

(52) U.S. Cl.
CPC ........... *G01N 33/0036* (2013.01); *F27B 9/40* (2013.01); *G01N 27/045* (2013.01); *G01R 3/00* (2013.01); *F27B 2009/3022* (2013.01)

(58) Field of Classification Search
CPC .... G01N 33/0036; G01N 27/045; G01R 3/00; F27B 2009/3022
See application file for complete search history.

(56) References Cited

U.S. PATENT DOCUMENTS

2021/0077197 A1*  3/2021  Govari .................. A61B 90/39

\* cited by examiner

*Primary Examiner* — Dominic E Hawkins
(74) *Attorney, Agent, or Firm* — Mark S Hubert

(57) ABSTRACT

An oxygen sensor for a gas, coal, oil or wood fired kiln that is orders of magnitude cheaper than the current state of the art oxygen sensors. It uses a $TiO_2$ tip sintered between and bridging a 1 mm spacing between a pair of 22 gauge Nichrome® series 90 round annealed resistance wires (0.64 mm diameter and having 0.648 Ohms/ft resistance). The Nichrome® 90 wires do not contact each other. One of the wires is a signal wire that resides down the center of an insulating sheath and the other wire is a ground wire that is wound around the outside of a high temperature ceramic insulating sleeve. The sensor needs no temperature compensation and exhibits an approximate 50,000 ohms of resistance change from a neutral (ambient) atmosphere and a fully reduced atmosphere.

5 Claims, 5 Drawing Sheets

OXYGEN SENSOR FOR HIGH TEMPERATURE KILNS AND METHOD OF FABRICATION

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to high temperature probes, and more particularly to high temperature gas fired kiln monitoring technology.

BACKGROUND

Striking and aesthetic visual effects can be achieved in fired clay pottery and ceramics by the use of metallic oxides on the object's surface then subjecting the fired object to cycles of decreased free oxygen in the kiln's atmosphere. This is known as reduction and produces different colors and visual effects at high temperatures as the metallic oxides on the surface of the fired objects give up oxygen and convert to their reduced, or more metallic form. The associated, vivid colors are impossible to achieve otherwise. However, to be able to control and repeat these effects the potter must be able to precisely monitor the levels of free oxygen in the kiln. With this information they can adjust the kiln dampers or fuel supply to maintain the reduction environment and still keep the kiln heating.

The installation of an oxygen sensor on a kiln allows the potter to monitor these reduction cycles. The current state of the art oxygen sensors for high temperature kilns use a core containing two porous electrodes which are made of zirconium/yttrium plated with a thin platinum conductive layer. This type of sensor requires an oxygen reference, which is housed in a long delicate ceramic tube. The cost of one of these oxygen probes is very high. Additionally, the highly corrosive nature of the firing atmosphere quickly degrades the probe's metallic parts, limiting its lifetime. To worsen matters, the probe is delicate and unable to withstand any shock or rough handling.

These sensors do not have long life spans, are very expensive and take up considerable space. Repair of a current oxygen probe is also expensive because it usually requires replacement of the probe's platinum coated wires. Operationally, they begin to work as soon as heated to red heat (1200 degrees F.) when they become sensitive to oxygen atoms. When there is a differential between the number of oxygen atoms sensed at the exposed end and the end sealed in the ceramic tube, a small voltage (emf) is produced and this is expressed in millivolts on a connected voltmeter meter.

Henceforth, an inexpensive, rugged and long-lasting oxygen probe for use in a high temperature, corrosive, non-electric kiln would fulfill a long felt need in the pottery and ceramics industry. This new invention utilizes and combines known and new technologies in a unique and novel configuration to overcome the aforementioned problems and accomplish this.

BRIEF SUMMARY

In accordance with various embodiments, an oxygen sensor for use in high temperature kilns is provided.

In one aspect, an inexpensive, quick and easy to fabricate oxygen sensor made from readily accessible materials and equipment is provided.

In another aspect, a durable oxygen sensor exhibiting a large range of change in resistivity in the working ranges of oxygen from a neutral to a fully reduced kiln atmosphere, at the elevated temperatures found in a ceramics kiln, is provided.

In yet another aspect, a rugged oxygen sensor providing only a minor change in resistivity due to a change in temperature up to 2400 degrees F.

In another aspect, a rugged oxygen sensor that does not require an oxygen reference, thus eliminating the need for a long delicate ceramic tube and a significant amount of platinum, is provided.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

DETAILED DESCRIPTION OF CERTAIN EMBODIMENTS

Figure 1:
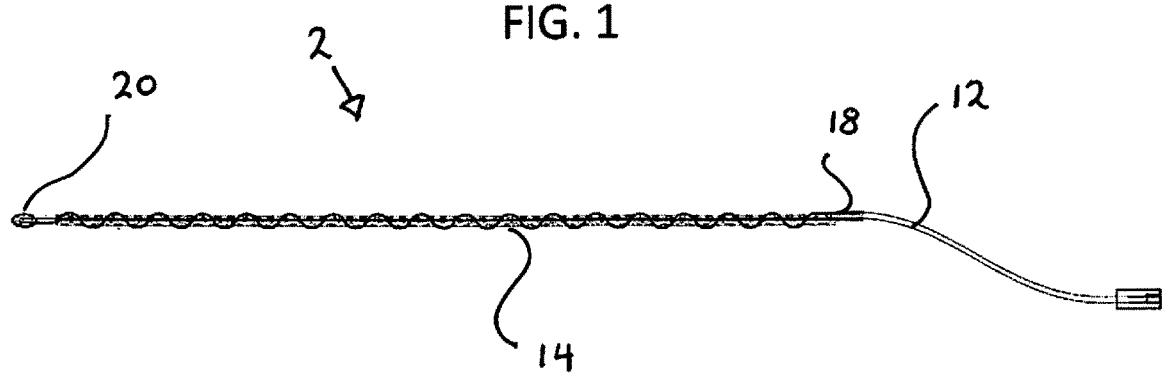
FIG. 1 is a side cross sectional view of the oxygen sensor.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first attachment could be termed a second attachment, and, similarly, a second attachment could be termed a first attachment, without departing from the scope of the inventive concept.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items.

The terminology used in the description of the inventive concept herein is for the purpose of describing particular embodiments only and is not intended to be limiting of the inventive concept. As used in the description of the inventive concept and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "gas kiln" or "gas fired kiln" refers to a kiln that uses a combustible gas such as propane or natural gas, or an ignitable fuel such as wood, coal, oil etc., to provide its heat source.

In the following description, for the purposes of explanation, numerous specific details are set forth in order to provide a thorough understanding of the described embodiments. It will be apparent to one skilled in the art, however, that other embodiments of the present invention may be practiced without some of these specific details. It should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Sensor Design and Structure

The present invention relates in general to oxygen sensors for pottery and ceramics kilns powered by hydrocarbon fuel, the three primary types of fuel being natural gas, propane and wood. However, other types of high temperature systems such as blacksmith forges and glass furnaces may also serve as an application for the disclosed invention. The oxygen sensor is easy, quick and cheap to fabricate, and does not require an oxygen reference, thus eliminating the long delicate ceramic tube and a significant amount of platinum which makes the current state of the art oxygen sensors, expensive delicate and short lived.®®

Figure 2:
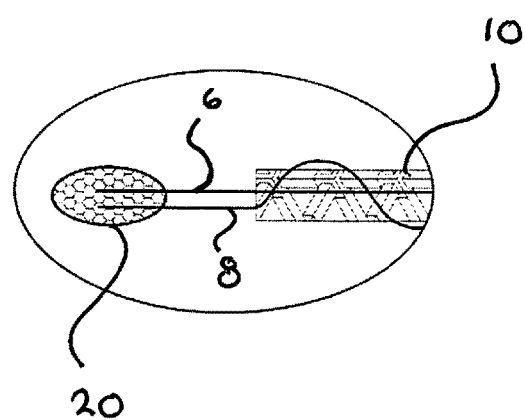
FIG. 2 is an enlarged view of the distal end of the oxygen sensor.
Figure 3:
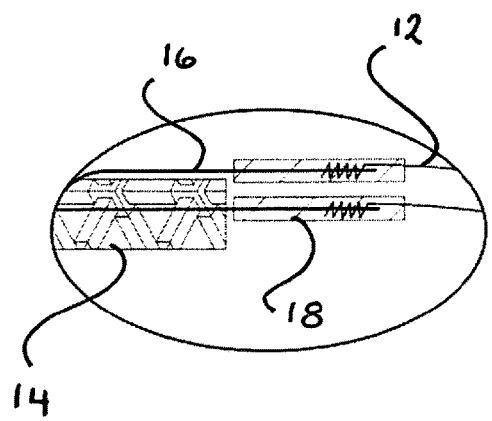
FIG. 3 is an enlarged view of the proximal end of the oxygen sensor.

Looking at FIGS. 1-3 the oxygen sensor 2 can be described for its proximal end to its distal end. At the proximal end is a pair of 24-gauge copper wires 12 that are mated at one end to an electrical connector (preferably an industry standard RJ 45 female to male connector) that is operationally connectable for plug in connection to any of the three different types of sensor signal interpretation and readout devices as described further herein. The other end of the copper wire pair 12 is connected to a pair of 22-gauge Nichrome® series 90 wires 16 at the proximal end of the sensor probe 14 and sealed with heat shrink tubing or another appropriate protective connector 18. These Nichrome series 90 wires 16 are an alloy consisting of 90% Nickel, and 10% Chrome, and were selected because they are ideally suited as a resistance wire heating alloy, with lower resistance due to its higher nickel content, a high melting point and fantastic resistance to high temperature oxidation as well as superior service life compared to other Nichrome wire types due to the excellent adhesion properties of its surface oxide.

The Nichrome® series 90 wires must not make physical contact. To accomplish this inner signal wire 6 is threaded into a high-temperature insulating sleeve 10 (preferably a ceramic sleeve) and the other Nichrome® series 90 wire 8 (the outside common wire) is loosely wound in a spiral around the sleeve 10 for the length of the probe 14, terminating at the measurement tip 20. The terminating Nichrome® series 90 wire pair at the distal end of the sensor 2 (the probe tip) must run parallel, terminate evenly, and be spaced apart with precision.

At the distal end of the sensor is the probe measurement tip 20. Here the terminating Nichrome® series 90 wire pair is bridged and covered with a very pure transition metal oxide which is Titanium Dioxide in the preferred embodiment. Both the wire spacing and the amount of wire covered by the Titanium Dioxide probe measurement tip 20 must be precise to insure probe-to-probe consistency.

Figure 8:
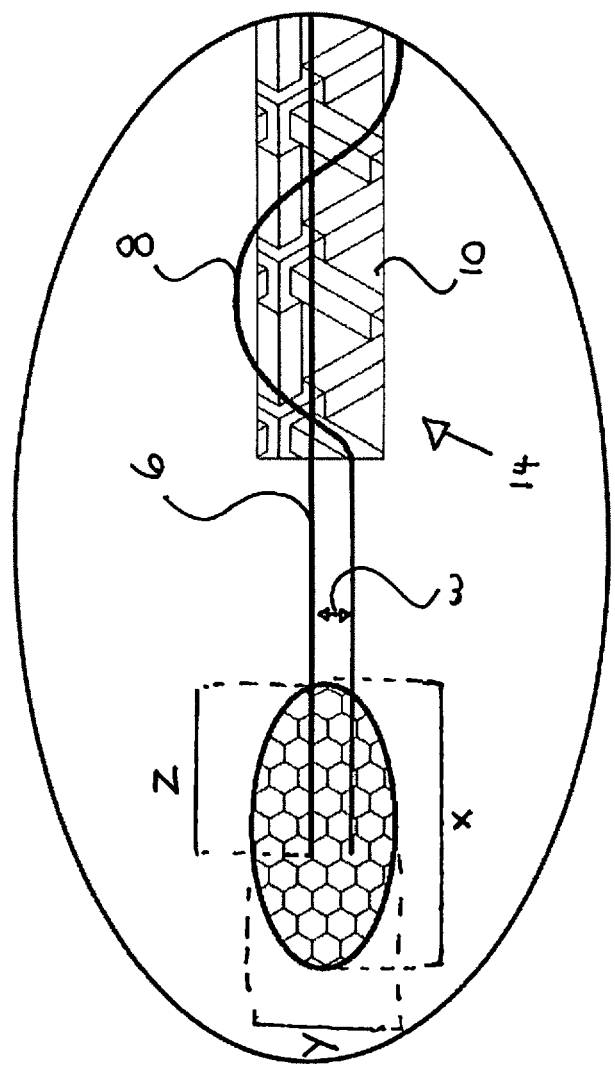
FIG. 8 is a side view of the oxygen sensor showing the $TiO_2$ bridge dimensions.

Looking at FIG. 8, it can be seen that the Nichrome® series 90 wire spacing, indicated by arrow W is 1 mm apart; the length of the Nichrome® series 90 wires that are coated or imbedded in the TiO$_2$ tip 20, indicated by distance line Z is 7 mm; the overall length of the TiO$_2$ tip 20, indicated by distance line X is 10 mm; and the diameter of the TiO$_2$ tip 20 is 4 mm. It is to be noted that all of these dimensions are plus or minus 2 mm.

Transition metal oxides such as Titanium Dioxide (being composed of oxygen atoms loosely bound to metal-oxygen compounds) when heated to above 1200 degrees F. and subject to a change in oxygen concentration, will have a change in its chemical properties that can be seen as a measurable change in resistivity when a voltage is applied. Here, the oxygen sensor 2 will change its resistivity from approximately 50,000 Ohms to 2 Ohms when gong from a neutral (ambient) atmosphere to a fully reduced atmosphere at 2300 degrees F.

Figure 5:
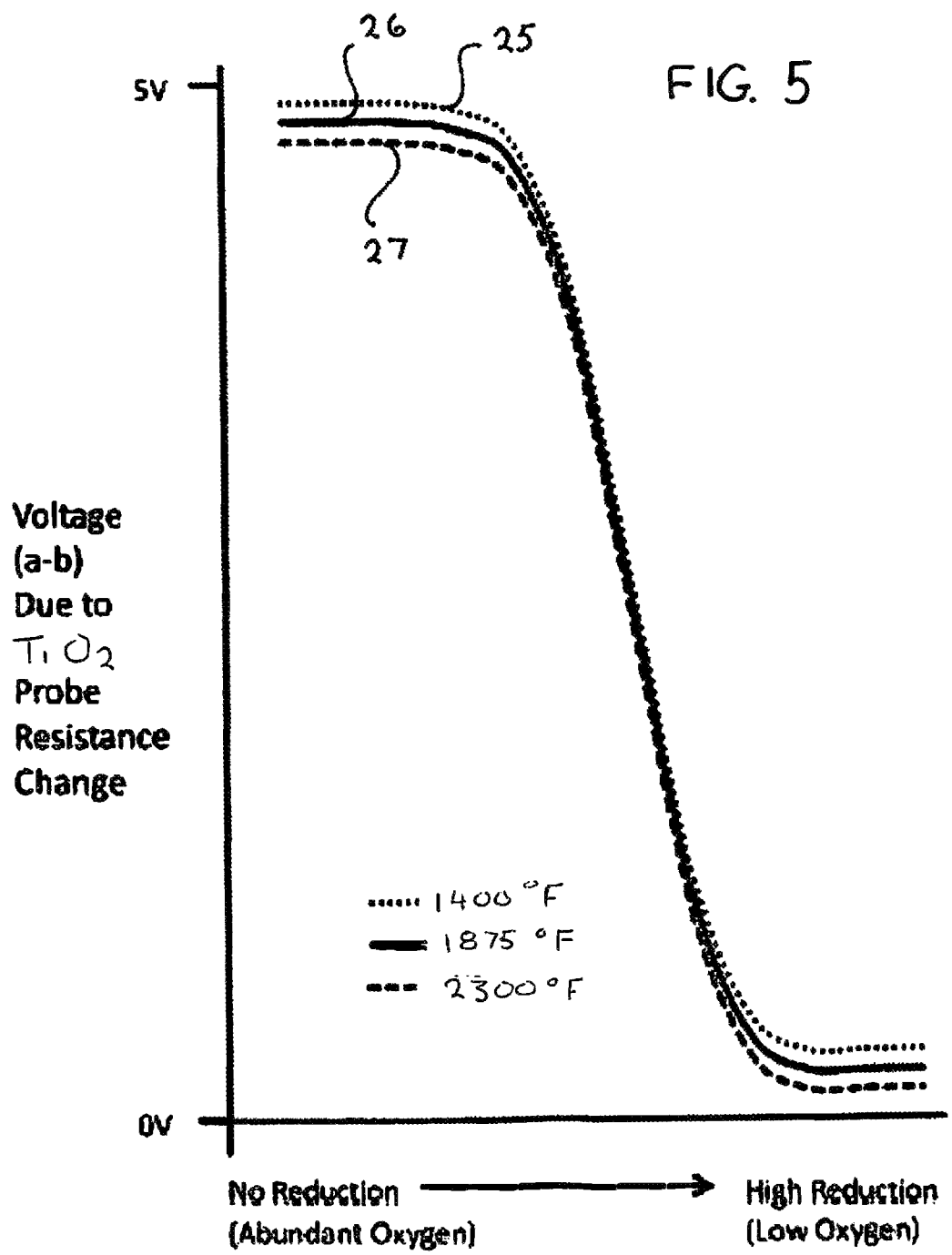
FIG. 5 is a graph showing the oxygen sensor responses to different applied temperatures.

Looking at FIG. 5 one can see a family of curves between 1400 and 2350 degrees F. showing that kiln temperature also has an effect on sensor resistivity. With a constant partial pressure of oxygen in the kiln environment, a rise in temperature will cause the resistivity and therefore voltage to decrease. Referring again to FIG. 5, curve 25 illustrates sensor response at 1400 F. Curve 26 shows sensor response at 1875 F, and curve 27 shows sensor response at 2350 F. It is important to note that the temperature correction represents less than 5% of the change in the resistivity due to the changing oxygen levels. When sensors are connected to a kiln atmosphere monitoring system (KAMS) as described in U.S. Pat. No. 10,067,002, it will compensate for the unwanted effect of temperature on the sensor(s) by applying a mathematical correction using the temperature of the kiln, however since the correction necessary is approximately only 5%, direct monitoring with an Ohmmeter or a DC powered circuit will give excellent indication of the reduction environment for the potter to visualize.

Fabrication

Several methods of the development of the $TiO_2$ tip have been employed, but the best method for the development of a rugged, shock resistant bridge is a cold fabrication method. Ground Titanium Dioxide is mixed with an organic binder, preferably a PVA glue into a slurry, with enough deionized, distilled water to thin the slurry for application. The 1 mm apart spaced Nichrome® series 90 wires at the distal end of the probe 14 are dipped into the slurry to ensure a length of at least 7 mm of the wires are coated. The slurry is then air dried by a low heat air gun similar to a hair dryer until the water in the PVA glue is evaporated leaving tip having a solid mass. This "dipping and drying" process is repeated until the overall length of the $TiO_2$ tip is approximately 10 mm in length and 4 mm in diameter. The dried tip 20 on the probe 14 receives no further treatment until it is ready for its first use in the kiln, with the $TiO_2$ being sintered by the kiln itself during its first use.

After installation into the kiln, the kiln temperature is raised to approximately 2300 degrees F. At approximately 400 degrees F. the binder and any residual water is burnt off, and by 1500 degrees F. the remaining $TiO_2$ is completely sintered so as to form a bridge between, and a coating thereon the final 7 mm of the 1 mm apart spaced Nichrome series 90 wires. The probe tip becomes very durable when used in the kiln. Early attempts to form the tip of the probe onto the Nichrome® series 90 wires was done by step by step sintering of the slurry onto the wire ends. This met with failure as the successive sintering processes left the tip 20 extremely fragile.

Installation

Figure 4:
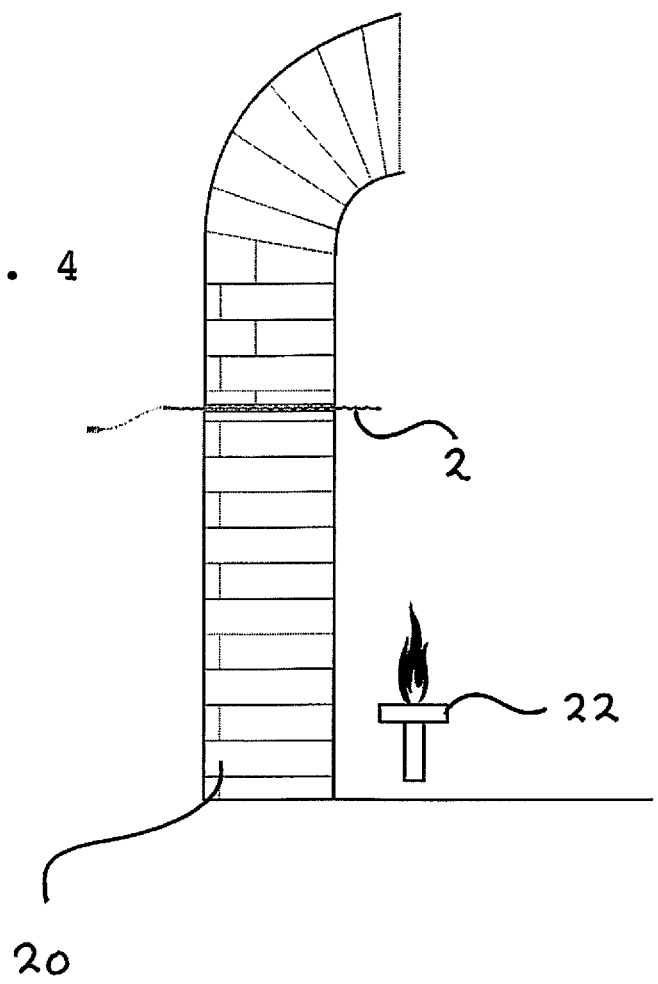
FIG. 4 is a side cross sectional view of the placement of the oxygen probe in a kiln.

Looking at FIG. 4 the oxygen sensor 2 can be seen installed in a kiln. For clarity only one sensor 2 is shown; however, installing multiple sensors is common as it provides more information related to different areas within the kiln, and provides a better overall result. Installation requires drilling an approximate ¼ inch hole into the kiln side 20 for each probe, and inserting the probe so the probe tip projects at least one inch into the kiln area. It must not be located too close to the gas burners 22. The physical structure of the specific kiln will often determine the practical location for the sensor or sensors. After initial installation a mechanical sealing of the void around the sensor 2 (both inside and outside) is required. Generally, this will be accomplished by the packing of a high temperature ceramic fiber. Wear is expected due to the corrosive nature of the kiln's environment, and the sensor will require replacement after multiple firings. Not shown in FIG. 2 is the electrical connection from the sensor 2 to the remainder of the system that provides a visual display of the oxygen content of the kiln's atmosphere, whether it be with an ohmmeter, a voltmeter/voltage divider circuit/power supply or a KAMS system.

Use

Figure 6:
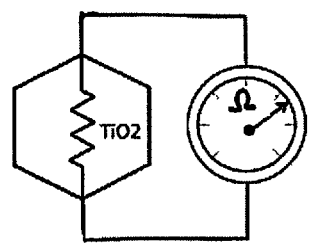
FIG. 6 is an electrical schematic of the oxygen sensor in an operational configuration with a powered ohmmeter.

When using the oxygen sensor, the status of the kiln's atmosphere may be interpreted in different ways by different oxygen concentration display devices. First as indicated in FIG. 6 the two probes of an ohmmeter may be connected to the ground and signal wires of the oxygen probe. The ohmmeter has an internal DC power source and a balancing resistor built in so it will directly read the changing resistivity of the sensor. It will initially be set in a scale that covers up to 50,000 Ohms (for a neutral atmosphere) and as the kiln's atmosphere approaches its maximum reduction, the ohmmeter's will have to have its scale reduced to be able to read 1-3 ohms (for a fully reduced atmosphere.) The swing to the lower resistivity will give a visual indication of the kiln's atmosphere condition.

Figure 7:
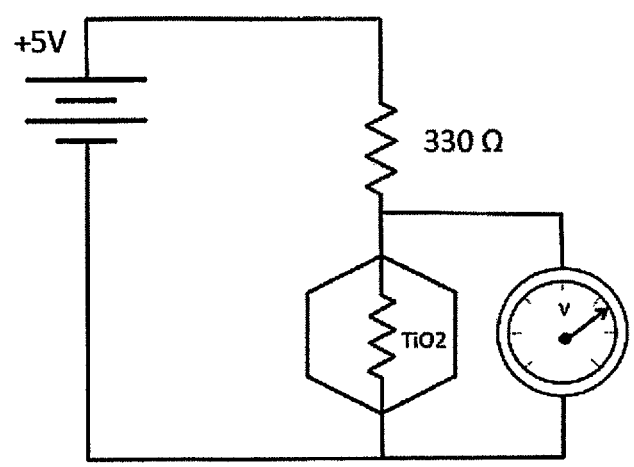
FIG. 7 is an electrical schematic of the oxygen sensor in an operational configuration with a simple voltage divider circuit.

In another external embodiment, as illustrated in the simple voltage divider circuit of FIG. 7 the ground and signal wires of the oxygen sensor may be connected in series with a 330 ohm reference resistor into a DC powered circuit (preferably 5 volt) with a voltmeter used to indicate the change in voltage as a function of the decreasing resistivity. When the chemical reaction occurs (once the probe is heated to at least 1200 F) the oxygen concentration decreases and the resistance across the $TiO_2$ sensor decreases, as does the voltage measured across the sensor. This circuit may be incorporated onto a PCB and interconnected to a KAMS. The connection only requires two wires—a signal wire and a common ground wire typically accomplished using industry standard RJ45 female to male interconnects.

This KAMS allows the Ceramicist to monitor oxygen levels in multiple locations of the kiln, and have the results analyzed, summarized, displayed and logged as real time values, summed and averaged across the kiln. For the average Ceramicist, this level of insight into the kiln's atmosphere is new, novel, and highly useful. Additionally, the KAMS system using the disclosed invention can be maintained indefinitely at a low cost because individual sensor replacement is relatively inexpensive and easy to perform.

Consequently, in view of the wide variety of permutations to the embodiments described herein, this detailed description and accompanying material is intended to be illustrative only, and should not be taken as limiting the scope of the inventive concept. What is claimed as the invention, therefore, is all such modifications as may come within the scope and spirit of the following claims and equivalents thereto.

What is claimed is:

1. An oxygen sensor for use with a high temperature hydrocarbon fired kiln, comprising:

a probe having a distal probe end and a proximal probe end, said probe made of an insulating sleeve with a signal wire made of an alloy consisting of 90% Nickel, and 10% chrome, said signal wire passing through the approximate center of said insulating sleeve and a common wire made of an alloy consisting of 90% Nickel, and 10% chrome, spirally wrapped around said insulating sleeve; said both signal wire and said common wire extending beyond said insulating sleeve and ending in a parallel, spaced configuration;

a sintered $TiO_2$ tip bridging between and onto said signal wire and said ground wire at said distal probe end, said sintered tip made of a mixture of $TiO_2$ powder mixed in a one to one ratio by volume with a PVA glue and heated to above 2200 degrees F.;

a first copper wire coupled to said first signal wire at said proximal end of said probe; and a second copper wire coupled to said common wire at said proximal end of said probe;

an electronic connector operably connected to said first wire and said second wire, said connector adapted for connection to an oxygen concentration display device.

2. The oxygen sensor of claim 1 wherein said $TiO_2$ sintered tip extends a minimum of 7 mm onto and between said signal wire and said common wire.

3. The oxygen sensor of claim 1 wherein said $TiO_2$ sintered tip has a minimum length of 10 mm.

4. The oxygen sensor of claim 1 wherein said signal wire and said common wire are parallel and a minimum of 1 mm apart at said distal probe end.

5. The oxygen sensor of claim 1 wherein;

said signal wire and said common wire are parallel and a minimum of 1 mm apart at said distal probe end;

said $TiO_2$ sintered tip extends a minimum of 7 mm onto and between said signal wire and said common wire;

said $TiO_2$ sintered tip has a minimum length of 10 mm; and said $TiO_2$ sintered tip has a minimum diameter of 4 mm.

* * * * *